| United States Patent [19] | [11] | 4,147,765 |
|---|---|---|
| Stephan et al. | [45] | Apr. 3, 1979 |

[54] PREPARATION OF ANTISERUM FOR QUANTITATIVE DETERMINATION OF X AND Y DEGRADATION PRODUCTS OF FIBRIN AND FIBRINOGEN

[75] Inventors: Wolfgang Stephan, Dreieichenhain; Ronald Kotitschke, Frankfurt am Main, both of Fed. Rep. of Germany

[73] Assignee: Biotest-Serum-Institut GmbH, Frankfurt am Main, Fed. Rep. of Germany

[21] Appl. No.: 706,050

[22] Filed: Jul. 16, 1976

[30] Foreign Application Priority Data

Jul. 18, 1975 [DE] Fed. Rep. of Germany ....... 2532151

[51] Int. Cl.$^2$ .................... A23J 1/06; G01N 31/02; G01N 33/16
[52] U.S. Cl. .................................. 424/12; 23/230 B; 195/103.5 A; 260/112 R; 424/85; 424/88; 424/101; 424/177
[58] Field of Search ................. 424/8, 12, 85, 88, 101, 424/177; 195/103.5 A; 260/112 R, 112 B; 23/230 B

[56] References Cited

FOREIGN PATENT DOCUMENTS 1362776   8/1974   United Kingdom ...................... 424/12

OTHER PUBLICATIONS

Marder, J. Biol. Chem., vol. 244, 1966, pp. 2111-2119.
Fisher, J. Lab. & Clin. Med., Vol. 70, 1967, pp. 903-922.

*Primary Examiner*—Anna P. Fagelson
*Attorney, Agent, or Firm*—Sprung, Felfe, Horn, Lynch & Kramer

[57] ABSTRACT

An antiserum for the quantitative determination of X and Y degradation products of fibrin and fibrinogen is produced by administering the purified degradation products to an experimental animal thereby to immunize said animal, drawing serum from said animal, contacting said serum with a plasma and separating the resultant precipitate, thereby to leave a supernatant liquid which constitutes said antiserum. The plasma may be a heparin, citrate, oxalate, ethylenediaminetetracetate or glutaraldehyde-treated plasma and as many as 12 or 15 precipitations may be made with the animal antiserum. The antiserum may be fractionated at any stage by adsorption on Sephadex modified dextran.

9 Claims, No Drawings

PREPARATION OF ANTISERUM FOR QUANTITATIVE DETERMINATION OF X AND Y DEGRADATION PRODUCTS OF FIBRIN AND FIBRINOGEN

BACKGROUND

The invention relates to an antiserum which reacts specifically with the early fibrin and fibrinogen degradation products (FDP) formed by the action of plasmin on fibrin and fibrinogen, referred to in the literature as "fibrinogen X (fg-X)" and "fibrinogen Y (fg-Y)", and it relates also to the preparation thereof.

The action of plasmin on fibrinogen produces fibrinogen degradation products which have acquired an increasing importance in the diagnosis and treatment of acquired hemorrhagic diatheses. Their detection can serve as a valuable diagnostic indication in a number of diseases. The most important diseases in which fibrinogen degradation products occur are listed summarily herewith:

1. Thrombotic diseases, such as venous thrombi, pulmonary embolism, myocardial infarction, coronary thrombosis;
2. Bacterial infections;
3. Carcinoma;
4. Kidney and liver diseases;
5. Obstetric complications.

The methods used heretofore for the recognition of FSP have been compared with one another in recent literature: MARDER, V. J., MATCHETT, M. O., SHERRY, S.: "Detection of serum fibrinogen and fibrin degradation products" Am. J. Med. 51: 71–82 (1971), THOMAS, D. P., NIEWIAROWSKI, S., MYERS, A. R. et al.: "A comparative study of four methods for detecting fibrinogen degradation products in patients with various diseases." N. Engl. J. Med. 283: 663–668 (1970), CARVALHO, A. C. A., ELLMAN, L. L., COLMAN, R. W.: "A comparison of the staphylococcal clumping test and an agglutination test for detection of fibrinogen degradation products." Am. J. Clin. Pathol. 62: 107–112 (1974).

All these methods have so many disadvantages that they have never been adopted into clinical routine testing.

In the proteolysis of fibrinogen with plasmin, the first recognizable degradation product is fg-X. It has a molecular weight of approximately 270,000. Fg-X can be brought to coagulation by thrombin, differing in this regard from all other degradation products formed from fibrinogen. As the degradation of fibrinogen by plasmin continues a fragment fg-Y and a fragment fg-D are formed from fg-X. Fg-Y has a molecular weight of 190,000, and is itself further broken down to an fg-D and an fg-E (MARDER, F. J.: "Immunologic structure of fibrinogen and its plasmin degradation products. Theoretical and clinical considerations." In Fibrinogen, ed. Laki, K., 1969, Marcel Dekker, Inc., New York, and Edward Arnold (Publishers, Ltd.), London, 339–358. PIZZO, S. V., SCHWARTZ, H. L., HILL, R. L., and McKEE, P. A.: "The effect of plasmin on the submit structure of human fibrin." J. Biol. Chem. 248: 4574–4583 (1973).

The fragments fg-D and fg-E are referred to as plasmin-resistant fragments of fibrinogen (BUDZYNSKI, A. Z., STAHL, M., KOPEC, M., LATALLO, Z., KOWALSKI, E.: "High molecular weight products of the late stage of fibrinogen proteolysis by plasmin and their structural relation to the fibrinogen molecule." Biochem. Biophys. Acta, 147: 313–323 (1967)). They comprise about 70% of the original fibrinogen molecule. The degradation products of fibrin (fb) resemble those of fibrinogen, except that fibrin-X (fb-X) is not coagulable by thrombin since it lacks the A and B peptides which are still present in fg-X. Also, the fibrinogen degradation products form soluble complex compounds with still-undegraded fibrinogen, as they do with fibrin monomers. The molecular weights of the complex compounds thus formed extend from 400,000 to 1,000,000.

The most important biological action of the fibrinogen degradation products is based on their antithrombin activity (such products are also referred to as "antithrombin IV"). The antithrombin activity of the early degradation products (fg-X and fg-Y) is about 10 times greater than that of the late degradation products (fg-D and fg-E). Electron microscope studies (BANG, N. V., FLETCHER, A. P., ALKJAERSIG, N. AND SHERRY, S.: "Pathogenesis of the Coagulation Defect Developing During Pathological Plasma Proteolytic (Fibrinolytic) Sates. III—Demonstration of Abnormal Clot Structure by Electron Microscopy." J. Clin. Invest. 41: 935–943 (1962) Part I) have shown that fibrin formed in the presence of fibrinogen degradation products differs greatly from normal fibrin, probably as a result of an abnormal polymerization.

The fibrin and fibrinogen degradation products are usually determined by immunological methods in which a fibrinogen antiserum is used. These methods are unsuitable for the determination of such degradation products, since the fibrinogen contained in the plasma also reacts with the fibrinogen antiserum. Since the early FDP's, such as fg-X and the larger complex compounds can be coagulated with thrombin and therefore are removed from the plasma in the coagulation procedure, the serum does not contain the entire spectrum of the fibrin and fibrinogen degradation products. Only the fragments Y, D and E and the smaller peptides are present in the serum, but not fragment X.

Antiserums against fg-D and fg-E are known. They show no cross reaction against antifibrinogen or with one another. They are used for distinguishing different fibrin and fibrinogen degradation products. Hitherto it has not been possible to prepare antiserums against fg-X and fb-X or against fg-Y and fb-Y, namely the early degradation products of fibrinogen. On account of the pronounced antithrombin action of these fibrin and fibrinogen degradation products, it would be desirable to have antiserums against these products, too, so as to be able to detect them directly in the plasma.

THE INVENTION

It has now surprisingly been found that a specific antiserum, suitable for diagnostic purposes, against the early fibrin and fibrinogen degradation products can be obtained by immunizing rabbits with fg-X or fb-X and fg-Y or fb-Y and/or a mixture of fg-X or fb-X and fg-Y or fb-Y, if, by means of sufficiently frequently repeated adsorptions with plasma or serum and fibrinogen, all unspecificities of the antiserum obtained are removed, especially the cross reaction with fibrinogen.

The invention involves the provision of an antiserum for the quantitative determination of the high molecular weight degradation products X and Y of fibrin and fibrinogen obtained by the action of plasmin on fibrin or fibrinogen.

The invention also extends to a method of preparing an antiserum against the high molecular weight degradation products fg-X, fg-Y, fb-X and fb-Y of fibrin and/or fibrinogen, which is characterized in that rabbits or other appropriate laboratory animals are immunized in a known manner, preferably with highly purified early degradation products of fibrin or fibrinogen, and the rabbit serums which are thus obtained are adsorbed with appropriate adsorption agents until the antiserum exhibits a reaction only with the early degradation products of fibrin or fibrinogen in Ouchterlony's immunodiffusion procedure, not with plasma, serum or fibrinogen. Suitable adsorption agents are heparin plasma, citrate plasma or plasmas which are stabilized with other known anticoagulants, such as, for example, oxalates, ethylenediaminetetracetic acid or mixtures of these plasmas. These plasmas must be obtained in such a manner that no fibrin or fibrinogen degradation products can form in them.

Better suited for the adsorption than the plasmas listed above are plasmas which have been polymerized with glutaraldehyde. The preparation of immunoadsorbents by the use of glutaraldehyde and protein solutions has been described by S. Avrameas (AVRAMEAS, S. AND TERWYNEK, T.: "The cross-linking of proteins with glutaraldehyde and its use for the preparation of immunoadsorbents." Immunochemistry 6: 53–66 (1966)). The protein solution which is used for the preparation of the immunoadsorbent can be of widely varying composition. It is important only that it contain all of the proteins which occur in human plasma, with the exception of high molecular weight fibrinogen degradation products.

The simplest and quickest method of preparing the specific antiserum against the early degradation products of fibrinogen uses plasma coupled by bromocyan to Sepharose. By analogy to works by CUATRECASAS, P. et al., Sepharose 4B (an agarose gel obtained when 4% agarose solution is made to form a gel in pearl form. Pharmacia, Uppsala, Sweden) is bound to protein solutions through bromocyan (BrCN). This procedure for the refinement and isolation of proteins, described by CUATRECASAS, is called "affinity chromatography". (CUATRECASAS, P., WILCHEK, M. and ANFINSEN, C. B.: "Selected enzyme purification by affinity chromatography." Proceedings of the National Academy of Sciences USA 61 (1968), pp. 635–643).

The antiserums used should have the highest possible antibody titer in the double diffusion procedure according to Ouchterlony (OUCHTERLONY, O. "Antigen-Antibody-Reaction in Gel" Archiv Kemie Mineral. Geol., Vol. 26 B, No. 14: 1–9 (1948)) against the early degradation products of fibrin and fibrinogen, even before the purification begins, since antibodies against the early degradation products are also lost during the frequently repeated adsorption processes. Therefore it is desirable to determine the titer of the serum of each individual rabbit prior to the adsorption, and to use only those serums whose titer is satisfactory. If fg-Y or fb-Y is used for the immunization of the laboratory animals, it is often impossible to obtain antiserums with an adequate titer. This is probably due to the fact that fg-Y and fb-Y are poorer antigens than fb-X and fg-X, or that, in the subsequent processing, too much of the antibodies formed are adsorbed from the antiserum during the adsorption. Consequently a pool is created from several selected rabbit serums and the adsorbent is added to the pooled antiserum. Antibodies which are not directed against the early fibrinogen degradation products are bound to the adsorbent and are then removed in an appropriate manner from the serum as described below. By the repetition of the adsorption one finally arrives at an antiserum that specifically reacts with the early fibrin or fibrinogen degradation products fg-X, fg-Y, fb-X and fb-Y.

The antiserum can then be used directly, but it is advantageous to fractionate it to increase the titer, i.e., to enrich the immunoglobulin content. It is even advantageous to obtain the immunoglobulin G fraction of the antiserums before the beginning of the adsorption processes. It has been found especially desirable to perform a chromatography of the serum on modified dextrans (Sephadex G 150 of Pharmacia Fine Chemicals AB, Uppsala, Sweden) and isolate the immunoglobulin G fraction from the fractions obtained in the gel chromatography. The isolated gamma globulin fraction is then adsorbed with suitable adsorbents until the fraction specifically reacts with none but the early degradation products of the fibrin or fibrinogen.

The antiserum obtained is especially suitable for the detection of high molecular weight degradation products of fibrin and fibrinogen in plasma, which has not been possible hitherto.

By means of this serum, the early degradation products of fibrin and fibrinogen can be determined quantitatively in a simple experimental arrangement. To this end, equal volumes of an appropriately diluted amount of the antiserum are added to an equal volume of a diluted plasma containing fibrinogen degradation products, and after an incubation time of 30 minutes the turbidity that develops is measured at an extinction E 436 Hg. From this measured value a blank value determination obtained with a normal plasma is subtracted. The remaining extinction value, with the aid of a reference curve, gives the content of fibrinogen degradation products in the tested plasma.

EXAMPLES

The invention will be explained by the following examples.

EXAMPLE 1

Each of 10 white New Zealand rabbits averaging 2.5 kg in weight were injected into the foot pads 5 mg of fg-X with complete Freund's adjuvant (CFA). Fg-X was produced as described in Marder, V. J., Shulman, N. R. and Caroll, W. R., "High molecular weight derivates of human fibrinogen produced by plasmin. I. Physicochemical and immunological characterization." The Journal of Biological Chemistry 244 (1966) No. 8, p. 2111–2119. On day 14 each rabbit received 5 mg fg-X+CFA i.m. and on day 28 5 mg fg-X+CFA subcutaneously. On day 56 each rabbit received 2 mg fg-X i.m. in the morning and 2 mg fg-X i.v. in the evening. On day 66 the rabbits were bled, giving approximately 50 ml blood. The pooled antiserum was heated for 60 Min at 56° C. 200 mg of lyophilized heparin plasma was added to 100 ml of rabbit serum and the mixture was let stand for 4 hours at 37° C. The the mixture was let stand for about 16 hours at about +4° C. The precipitate was separated by centrifugation. The supernatant liquid was again treated with heparin plasma (200 mg per 100 ml), incubated for 4 hours at 37° C., and then again let stand for 16 hours at +4° C., and the precipitate that formed was again removed by centrifugation. The outcome of each of these adsorption steps was tested by Ouchterlony's immunodiffusion technique. The adsorption process that has been described is to be repeated until the antiserum shows a precipitation line in the immunodiffusion test with the early fibrin and fibrinogen degradation products, but no longer reacts with fibrinogen or with a normal plasma or normal serum. Experience indicates that the adsorption has to be repeated from 12 to 15 times before the antiserum is specific.

30 ml of antiserum was passed through a column K 50/100 of Pharmacia Fine Chemicals, Uppsala, Sweden, containing Sephadex G 150, bed volume 1500 ml. Elution was effected with 1400 ml of 0.1 M sodium chloride solution. The first peak appeared after 550 ml and contained 350 ml. The second peak with 130 ml containing the immunoglobulin G fraction of the antiserum was brought to a protein concentration of about 5% by means of a ultrafiltration cell Model 402 of "Amicon B. V.", Holland, or Amicon Corp., Lexington, Mass.

In the following example, adsorptions are described which have produced particularly good results. The conditions specified with regard to the adsorption time, adsorption temperature and the amount of adsorption plasma used can vary widely without resulting in any other than the results described.

EXAMPLE 2

50 ml of antiserum was passed through a column K 50/100 of Pharmacia Fine Chemicals, Uppsala, Sweden, containing Sephadex G 150, bed volume 1500 ml. Elution was effected with 1500 ml of 0.1 M sodium chloride solution. The second peak appeared after 580 ml and contained 165 ml, containing the immunoglobulin G fraction. This fraction was brought to a protein concentration of about 5% by means of a ultrafiltration cell Model 402 of Amicon B.V. 200 mg of lyophilized heparin plasma was added to 100 ml of this fraction, and the adsorption was performed as described in Example 1. The adsorption was repeated until the treated fraction still reacted with the early fibrin and fibrinogen degradation products, but no longer reacted with fibrinogen, normal plasma and/or normal serum. Then the antiserum fraction adsorbed with heparin plasma was again chromatographed on modified dextran (Sephadex G 150) and the fraction containing immunoglobulin G was pooled and concentrated to a protein value of 5%.

In the following example the preparation of a plasma polymerized with glutaraldehyde is described.

EXAMPLE 3

For the adsorption of the rabbit antiserum, an immunoadsorbent was prepared as follows. 100 ml of ion exchange resin plasma was adjusted to a pH of 7.0 with 1 M acetate buffer, pH 5.0. 30 ml of a 25% solution of glutardialdehyde was added to 100 ml of this plasma, drop by drop, with stirring, at room temperature. The mixture was let stand for 3 hours at room temperature, and the precipitate was separated by centrifugation. The precipitate was suspended with 100 ml of physiological sodium chloride solution and stirred for 15 minutes at room temperature. Then the mixture was centrifuged and the precipitate was again suspended with physiological saline solution, stirred for 15 minutes at room temperature, and again centrifuged. This washing procedure was repeated once again. The polymerized plasma was then forced through a fine sieve. The above-described washing procedure was then repeated three more times with the strained polymerized plasma.

1.5 g of the plasma polymerized with glutaraldehyde was added to 100 ml of rabbit serum, and the mixture was stirred for 1 hour at room temperature. Then the mixture was let stand for about 16 hours at about +4° C. The precipitate was separated by centrifugation. The supernatant liquid was then again treated with glutaraldehyde-polymerized plasma as it was in the above-described first adsorption. This adsorption procedure must be repeated until the antiserum still shows a precipitation line in the immunodiffusion with the early fibrin and fibrinogen degradation products, but no longer reacts with fibrinogen or a normal plasma or normal serum.

The specific antiserum can then be further processed as described in Example 1 to increase the titer against the early degradation products of fibrin and fibrinogen. As described in Example 2, it is also possible to chromatograph the rabbit serum on Sephadex G 150 prior to the adsorption, and to adsorb the isolated immunoglobulin G fraction with the polymerized plasma.

EXAMPLE 4

100 ml of Sepharose 4B is stirred with 100 ml of water. To this suspension, 10 g of BrCN dissolved in 100 ml of water is added, with stirring, at room temperature. The pH value was adjusted to pH 11 with 4N sodium hydroxide and was maintained at this pH for 30 minutes by the further addition of sodium hydroxide. The suspension was then washed on a suction filter with 800 ml of 0.1 M $NaHCO_3$ solution of pH 8.9. Then the activated Sepharose was suspended in 100 ml of 0.1 M $NaHCO_3$ of pH 8.9, and stirred with 10 g of fresh plasma for 24 hours at about +4° C. This mixture was then placed in a chromatography tube and washed with 0.9% sodium chloride solution until no more protein was eluted. 5 ml of the rabbit antiserum was then chromatographed on the column. The eluate was collected in fractions, the protein fractions were combined, and then concentrated to a protein content of about 5%.

The outcome of this affinity chromatography was tested by the immunodiffusion technique of Ouchterlony, as described in Example 1.

The affinity chromatograph was repeated until the antiserum specifically reacted with the early fibrin and fibrinogen degradation products in the immunodiffusion test.

The conditions described in this example can be varied with regard to the quantity ratios specified and the other parameters given, without thereby producing substantially different results.

It will be appreciated that the instant specification and examples are set forth by way of illustration and not limitation, and that various modifications and changes may be made without departing from the spirit and scope of the present invention.

What is claimed is:

1. A method for the preparation of an antiserum against the degradation products X and Y of fibrin and fibrinogen which are obtained by the action of plasmin on fibrin or fibrinogen, comprising administering the purified degradation products to an experimental animal thereby to immunize said animal, drawing serum from said animal, and a plurality of times contacting said serum with a human plasma and separating the resultant precipitate, and repeating the contact and separation until there is left a supernatant liquid which constitutes said antiserum and is specific to X and Y.

2. The method of claim 1, wherein the plasma is one which has been treated with glutaraldehyde.

3. The method of claim 1, wherein the plasma is one which has been coupled to bromocyan-activated agarose.

4. The method of claim 1, including the subsequent step of contacting the antiserum with modified dextran to adsorb an immunoglobulin G fraction and eluting said fraction from the modified dextran.

5. The method of claim 1, wherein the animal serum prior to contact with the plasma is fractionated to obtain an immunoglobulin G fraction and said fraction is contacted with the plasma.

6. The method of claim 1, wherein the plasma is a heparin, citrate, oxalate or ethylenediaminetetracetate plasma or a glutaraldehyde-treated plasma, and the supernatant liquid antiserum is contacted with said plasma and the precipitate withdrawn about 12 to 15 times.

7. The method of claim 1, wherein the degradation product administered is fibrin-X or fibrinogen-X and wherein prior to or after contact with the plasma the antiserum is contacted with modified dextran to adsorb an immunoglobulin G fraction and the fraction is eluted from the modified dextran.

8. A purified antiserum for the quantitative determination of high molecular weight degradation products X and Y of fibrin and fibrinogen, produced by the process of claim 1.

9. A process for the quantitative determination of high molecular weight degradation products X and Y of fibrin and fibrinogen in a patient's blood, comprising mixing said blood with the antiserum of claim 8, and measuring the resultant turbidity, the turbidity increasing with an increase in the amount of said degradation products in the blood sample.

* * * * *